US008693626B2

(12) United States Patent
Bare et al.

(10) Patent No.: US 8,693,626 B2
(45) Date of Patent: Apr. 8, 2014

(54) SOLID MATERIAL CHARACTERIZATION WITH X-RAY SPECTRA IN BOTH TRANSMISSION AND FLUORESENCE MODES

(75) Inventors: Simon Russell Bare, Elk Grove Village, IL (US); Shelly D Kelly, Bolingbrook, IL (US); Wharton Sinkler, Des Plaines, IL (US); Nan Greenlay, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 182 days.

(21) Appl. No.: 13/162,762

(22) Filed: Jun. 17, 2011

(65) Prior Publication Data
US 2012/0321039 A1 Dec. 20, 2012

(51) Int. Cl.
*G01N 23/223* (2006.01)
*G01T 1/36* (2006.01)
(52) U.S. Cl.
USPC .............................................. 378/49; 378/45
(58) Field of Classification Search
USPC .......................................................... 378/49
See application file for complete search history.

(56) References Cited

U.S. PATENT DOCUMENTS

| | | | | |
|---|---|---|---|---|
| H922 H | * | 5/1991 | Kirkland et al. | 378/45 |
| 5,294,579 A | * | 3/1994 | Ohashi et al. | 502/66 |
| 5,354,933 A | * | 10/1994 | Ohashi et al. | 585/419 |
| 7,197,110 B2 | | 3/2007 | Riess et al. | |
| 7,206,375 B2 | * | 4/2007 | Chen et al. | 378/51 |
| 7,649,975 B2 | | 1/2010 | Boyden et al. | |
| 8,268,048 B2 | * | 9/2012 | Subramaniam et al. | 95/138 |
| 2009/0161829 A1 | | 6/2009 | Chen et al. | |
| 2010/0213406 A1 | * | 8/2010 | Buonassisi et al. | 252/181.6 |
| 2010/0320388 A1 | | 12/2010 | Rosenberg | |

OTHER PUBLICATIONS

Muñoz et al.; (May 5, 2011) "Structural properties and reduction behavior of novel nanostructured pd/gadolinia-doped ceria catalysts with tubular morphology"; Source: Journal of Physical Chemistry C, vol. 115, No. 17, pp. 8744-8752.
Grolimund et al.; (Oct. 8, 2004) "Shedding new light on historical metal samples using micro-focused synchrotron X-ray fluorescence and spectroscopy"; Source: Spectrochimica Acta—Part B Atomic Spectroscopy, vol. 59, No. 10-11, pp. 1627-1635, 17th International Congress on X-Ray Optics and Microanalysis.
McHugo et al.; (Mar. 1, 2000) "Synchrotron-based impurity mapping"; Source: Journal of Crystal Growth, vol. 210, No. 1, pp. 395-400.
Nawani et al.; (Sep. 11, 2007) "Surface modification of nanoclays by catalytically active transition metal ions"; Source: Langmuir, vol. 23, No. 19, pp. 9808-9815.

* cited by examiner

*Primary Examiner* — Hoon Song
*Assistant Examiner* — Danielle Fox
(74) *Attorney, Agent, or Firm* — Mark Goldberg

(57) ABSTRACT

Methods are disclosed utilizing synchrotron X-ray microscopy including x-ray fluorescence and x-ray absorption spectra to probe elemental distribution and elemental speciation within a material, and particularly a solid that may have one or more elements distributed on a solid substrate. Representative materials are relatively homogeneous in composition on the macroscale but relatively heterogeneous on the microscale. The analysis of such materials, particularly on a macroscale at which their heterogeneous nature can be observed, provides valuable insights into the relationships or correlations between localized concentrations of elements and/or their species, and concentrations of other components of the materials. Sample preparation methods, involving the use of a reinforcing agent, which are advantageously used in such methods are also disclosed.

16 Claims, 3 Drawing Sheets

SOLID MATERIAL CHARACTERIZATION WITH X-RAY SPECTRA IN BOTH TRANSMISSION AND FLUORESENCE MODES

FIELD OF THE INVENTION

The present invention relates to the analysis of solids by x-rays, and more particularly by using a combination of microbeam x-ray absorption spectroscopy (XAS) and microbeam x-ray fluorescence (XRF). The invention also relates to the analysis of solids, including the preparation of samples of solids, such as catalyst particles that exhibit heterogeneity on the microscale.

DESCRIPTION OF RELATED ART

Major and trace elements in material samples can be analyzed on the basis of their characteristic interactions with x-rays. For example, spectra of a given element in a sample may be obtained using x-ray absorption spectroscopy (XAS), upon scanning the incident x-ray energy, using a monochromator, through an absorption edge of the element. When the incident x-ray energy matches the binding energy of an electron of the element, the probability for x-ray absorption increases dramatically. This causes a drop in the transmitted x-ray intensity, which is characteristic of the absorption edge.

The absorption edge can be measured directly from the log ratio of the incident to transmitted x-ray intensities (transmission mode) or otherwise from the ratio of the fluorescent to incident x-ray intensities (fluorescence mode). Every element has a unique set of absorption edges that correspond to the different binding energies of its electrons, and it is this principle that establishes the element selectivity of x-ray absorption spectroscopy (XAS) and x-ray fluorescence (XRF). XAS includes both extended x-ray absorption fine structure (EXAFS), which provides local atomic structure, and x-ray absorption near edge structure (XANES), which provides coordination geometry and valence state information. The information contained in XANES, close to the absorption edge, probes the allowable electronic transitions from the ground state to the excited state. The information contained in EXAFS, well above the absorption edge, probes the interaction between the excited photoelectron and neighboring atoms.

According to the principle underlying x-ray fluorescence (XRF), the absorption of an x-ray by an atom results in the excitation of a core electron to an excited state, leaving behind a hole, termed a "core-hole." The excited state of the atom is short-lived, and the core-hole is filled by an electron that releases an x-ray as it transitions from an energy level near the Fermi level to the core hole. This results in the fluorescence of a characteristic x-ray having an energy that is unique for each transition and is termed fluorescent radiation. Because the energy of the emitted photon is characteristic of a transition between specific electron orbitals in a particular element, the energy of the fluorescent x-ray can be used to detect the elements in a sample, with the intensity of the fluorescence being proportional to the elemental concentration in the sample.

XAS measurements require a broad band of x-ray energies, and the intensity of monochromatic radiation that can be obtained from conventional electron beams and x-ray tubes is too low for most XAS measurements. An important development in this analytical technique was therefore based on the recognition that electron storage rings used in high energy physics can serve as an extremely intense source of x-rays. When electrons are accelerated by changing their direction with a magnetic field, they radiate a broad spectrum of radiation. Groups of electrons can be stored and synchronized in a circular orbit, causing radiation to be emitted at each bend. This gives rise to synchrotron radiation, in which an experimental beamline is placed at each bend around the electron storage ring.

The analytical capabilities of synchrotron x-rays represent a promising field of ongoing investigation. The art continues to develop and refine methods for characterizing materials, and particularly those, such as catalysts, that rely on the presence of elements at low concentrations. The particular characteristics of these elements, for example their oxidation state and the neighboring atoms with which they are bonded, are major factors in determining the performance of such materials.

SUMMARY OF THE INVENTION

The present invention is associated with the discovery of uses of synchrotron x-ray microscopy, including both microbeam x-ray fluorescence (XRF) and microbeam x-ray absorption spectroscopy (XAS), to probe elemental distribution and elemental speciation within a material, respectively, and particularly a solid that has one or more elements distributed on a solid substrate. Representative materials are advantageously those that are relatively heterogeneous on the microscale, such that their element concentrations can deviate on the microscale, relative to their corresponding bulk material concentrations, by greater than 1%, and often greater than 5%. These deviations from the bulk concentrations may be observed, for example, over a sample dimension of less than 100 μm or in some cases less than 3 mm (representative of a typical catalyst particle size).

Macroscale-representative samples of the material are those of a sufficient discreet sample size (e.g., size of an individual particle or a cut section of a particle) having a maximum deviation of less than 5%, and often less than 1%, with respect to the bulk concentrations (e.g., measured in terms of percentage by weight) of elements in the material. Macroscale-representative samples also include those that are macroscale-representative over at least one dimension (e.g., length) or over two dimensions (e.g., both length and width, or surface area), over which deviations above these maximum values with respect to the bulk concentrations are not observed. For example, a macroscale-representative sample might not necessarily be macroscale-representative over at least one other dimension (e.g., thickness) but macroscale-representative with respect to its length or cross-sectional surface area. Macroscale-representative samples advantageously have at least one dimension that is sufficiently large for the observation of local heterogeneity of the sample, over that dimension. Macroscale-representative samples are therefore generally distinguishable, for example, from fine powders, which do not have any dimension sufficient for observing local heterogeneity over a scale of hundreds of microns or even millimeters.

The analysis of such materials, particularly on a macroscale over which the extent of their heterogeneity may be observed, for example by XRF mapping (e.g., over two or three dimensions), provides valuable insights into the relationships or correlations between localized concentrations of elements and/or their species, and concentrations of other components of the materials and/or their species. Such analytical information, which is often paramount to the overall performance characteristics of the material, provides significant advantages over results obtained from conventional analyses performed, for example, on a ground powder of the material sample, in which this spatial information is lost. The methods described herein are also applicable to solid materials that may be homogeneous on both the macroscale and microscale, and even on the molecular level, for example in the case of a zeolitic material having a regular crystalline structure.

Aspects of the invention also relate to the preparation of macroscale-representative samples of solid materials. In exemplary preparation methods, the sample is combined with a reinforcing agent such as a polymeric material (e.g., an epoxy resin), that allows the sample to be made with at least one sufficiently small dimension (e.g., thickness) for synchrotron x-ray analysis. Such preparation methods apply especially to porous, solid catalysts that generally cannot be cut to such a dimension without mechanical degradation (e.g., crumbling). Representative thicknesses of samples prepared in this manner are commensurate with the spatial resolution required to observe the heterogeneity, as well as the penetration depth of the x-rays, which depends on the elemental composition of the sample. If the concentration(s) of the element(s) to be measured in the sample is/are sufficient for transmission mode experiments, then the sample thickness should be suitable for allowing passage of the incident x-ray radiation (in absorption mode), without introducing excess interference that can be observed at greater thicknesses. The sample should also be thin enough such that the integrated signal over the entire thickness of the sample is representative of one component of the sample. Spatial resolution requirements may also dictate the sample thickness. Often, the limited number of atoms of an element of interest within a small volume probed by the x-ray beam results in the use of fluorescence mode XAS measurements. In this case, the sample can be of any thickness, as long as the penetration depth of the x-ray beam is sufficiently short such that only a single component of the sample is probed. Representative sample thicknesses, including thicknesses of samples of low Z-materials where the entire depth of the sample is to be measured, are generally less than about 500 µm (e.g., from about 5 µm to about 500 µm), typically less than about 200 µm (e.g., from about 5 µm to about 200 µm), and often less than about 100 µm (e.g., from about 5 µm to about 100 µm).

At least one other dimension of the sample (e.g., cylindrical diameter), however, is generally at least about 200 µm, typically at least about 500 µm and often at least about 1 mm. By maintaining the solid material with at least one dimension on the macroscale and with good mechanical integrity, the analytical data obtained from one or more x-ray analyses, particularly with respect to the distribution and speciation of one or more elements in the sample, can be readily correlated with scanning electron microscopy (SEM) data, allowing additional valuable data to be obtained. The ability to effectively analyze samples, and especially catalyst particles, on the microscale as correlated to the macroscale represents a significant aspect of the invention, which is related to the sample preparation methods described herein. Due to the potentially heterogeneous nature of such solids on the microscale, the analysis of macroscopically averaged samples, such as ground powders in bulk, does not convey much valuable information relating to the environment in which certain elements are located. It is this environment, however, that determines such special features as oxidation state and local coordination geometry that often play a pivotal role in the performance of the solid material for a given application (e.g., catalysis of a given chemical reaction).

Particular embodiments of the invention are directed to methods for analyzing a solid, which may comprise one or more elements (e.g., as a dispersed phase) distributed in a solid substrate (e.g., as a continuous phase). Representative methods comprise (a) preparing a sample of the solid (e.g., a macroscale-representative sample), (b) obtaining or determining the distribution of the one or more elements from spatially resolved x-ray fluorescence (XRF) analysis of the sample, and (c) obtaining or determining the speciation of the one or more elements from spatially resolved x-ray absorption spectroscopy (XAS) analysis of the sample. According to these methods, the source of x-rays for steps (b) and (c) is synchrotron radiation. The macroscale-representative sample may be thin or may provide limited x-ray penetration in one dimension but may be macroscale-representative in one or two other dimensions. Generally, the distribution and speciation determinations are made on the nanometer to micron scale using microbeam XRF and XAS analyses.

The XAS analysis comprises x-ray absorption fine structure (XAFS), extended x-ray absorption fine structure (EXAFS), x-ray absorption near edge structure (XANES), or a combination thereof. Such analyses may be used to determine information about the local environment(s) of one or more element(s) of the sample, including the one or more distributed (e.g., dispersed) elements and/or one or more elements of a component of the solid substrate. Such information includes the oxidation state(s) of the element(s), the atom(s) bonded to the element(s), and/or the local coordination geometry of the element(s).

According to particular embodiments, in step (b), the distribution of the one or more elements is obtained by analyzing a 2-dimensional elemental specific microbeam XRF signal of the sample. According to other particular embodiments, step (b) comprises, in addition to obtaining the distribution of the one or more elements from x-ray fluorescence (XRF) analysis, also obtaining the distribution of one or more components of the solid substrate. According to yet more particular embodiments, step (b) further comprises (i) correlating the distribution of the one or more elements with the distribution and/or speciation of the one or more components of the solid substrate or (ii) correlating the speciation of the one or more elements with the distribution and/or speciation of the one or more components of the solid substrate. Any of the x-ray data obtained at the nanometer to micron length scale over a macroscale-representative sample, including distribution(s) of the various elements, may also be cross-correlated with other analytical techniques for evaluating solid materials such as catalysts, which may be heterogeneous on the microscale but homogeneous on the macroscale, as described above. Such analytical techniques include SEM.

Further embodiments of the invention are directed to methods for analyzing a catalyst. The methods comprise obtaining spatially resolved x-ray absorption spectra in both the fluorescence and transmission modes, on a solid sample that is representative of the catalyst on the macroscale. "Spatially resolved" x-ray absorption spectra (from "spatially resolved" x-ray analyses including spatially resolved XRF and spatially resolved XAS) provide resolution over a size range from about 10 nanometers (nm) to about 10 microns (µm), and such spectra are normally obtained at multiple, discreet locations of the solid sample, in order to generate valuable characterizing information as described in greater detail below. Typically, the x-ray spectra are obtained over an area of the solid sample ranging from about 5,000 µm$^2$ to about 100,000 µm$^2$, and often from about 10,000 µm$^2$ to about 50,000 µm$^2$.

These and other embodiments and aspects relating to the present invention are apparent from the following Detailed Description.

BRIEF DESCRIPTION OF THE DRAWINGS

Some embodiments of the invention are illustrated by way of example, and not by way of limitation, in the accompanying figures.

DETAILED DESCRIPTION

Figure 1:
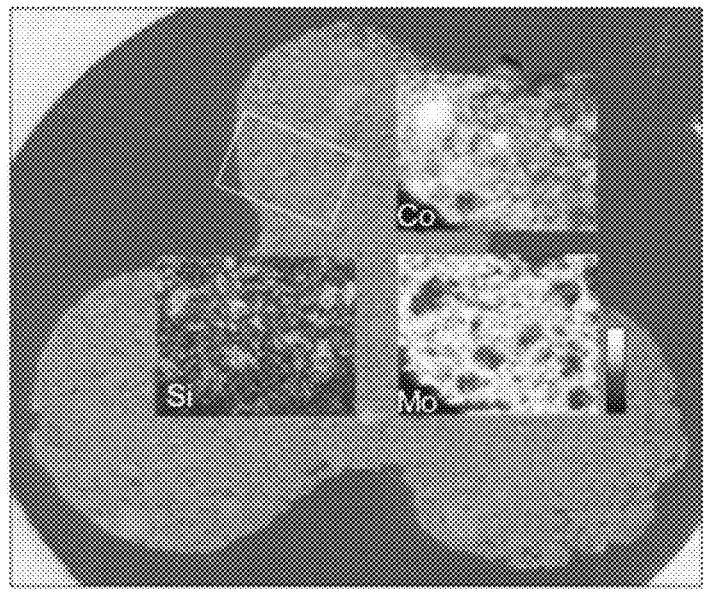
FIG. 1 provides x-ray fluorescence (XRF) images of samples of formed, supported metal catalysts, namely a prototype catalyst and a reference catalyst, as cylindrical extrudates used in hydroprocessing applications. Both catalysts that were analyzed contained cobalt and molybdenum as catalytic metals, distributed in a solid substrate of refractory inorganic metal oxide.
Figure 1:
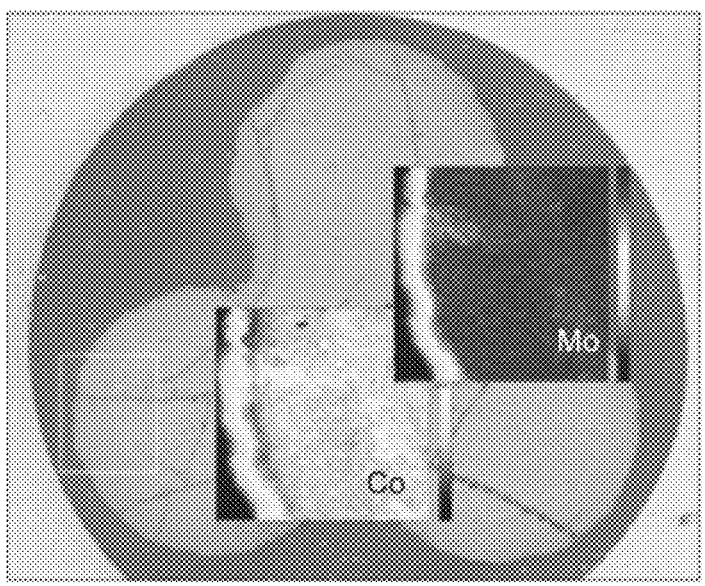

Aspects of the invention are associated with analytical techniques that utilize x-rays to characterize solid materials in a number of meaningful ways, and advantageously the samples analyzed are representative of the solid material, for example a formed solid catalyst particle, as it is used in practice. Representative analytical methods utilize microprobe x-ray absorption spectra in both the fluorescence and transmission modes to determine the valence state and coordination geometry (XANES) and/or local atomic structure (EXAFS), optionally in combination with microprobe x-ray fluorescence maps to determine elemental concentrations and the correlation of different elements with different constituents of the sample. The use of both analytical techniques based on x-rays provides important advantages in terms of obtaining information that conventional methods and combinations (e.g., the combination of scanning electron microscopy (SEM) and bulk x-ray absorption fine structure (XAFS)) do not communicate. Such information includes the correlation between the distribution of one or more species (i.e., determined from XAS speciation) of dispersed phase elements (e.g., metals such as cobalt and molybdenum, as catalytic metals) and the distribution of one or more continuous phase or matrix components (e.g., metal oxides such as silica and alumina, as catalyst support materials). Speciation refers to the determination of any of a number of characteristics of an element, as it exists in the sample, including oxidation state of the element(s), atom(s) bonded to the element(s), and/or the local coordination geometry of the element(s). The use of synchrotron radiation as an intense source of x-rays, according to the methods described herein, is particularly advantageous in terms of allowing the x-ray beam to be focused to a nanometer to micron length scale, with sufficient intensity to enhance sensitivity of the analytical method to a particular, targeted element (e.g., a catalytic metal) at low concentrations.

Particular embodiments of the invention are therefore directed to methods for analyzing a solid comprising one or more elements (e.g., metals, including catalytic metals of a dispersed phase) distributed in a solid substrate. Representative solid substrates (including those comprising matrix/binder materials used in catalysts), comprise a substrate material selected from carbon, inorganic metal oxides, and mixtures thereof. The distributed (dispersed) elements are generally each present in the solid and sample in minor amounts. In representative embodiments, each distributed element is present generally in an amount of less than about 10% (e.g., from about 10 ppm to about 10%) by weight, typically in less than about 5% (e.g., from about 100 ppm to about 5%) by weight, and often less than about 3% (e.g., from about 0.3% to about 3%) by weight. The solid substrate, on the other hand, is present generally in a major amount. In representative embodiments, the solid substrate is present generally in an amount of greater than about 30% (e.g., from about 30% to about 100% by weight), typically in greater than about 50% (e.g., from about 50% to about 99%) by weight, and often greater than about 75% (e.g., 75% to about 97%) by weight.

A representative solid is a catalyst particle, which may be of any conventional shape including cylindrical (e.g., as an extrudate), spherical (e.g., as an oil dropped particle), granular, trilobe, etc. Possible metals and combinations of metals, as elements that are distributed on the solid substrate (e.g., a matrix/binder material of a catalyst), include those of any of Groups 4-13 of the Periodic Table. Representative metals include noble metals such as Pt, Pd, Au, Ru, Re, Ag, Os, and Rh, as well as various other metals known to catalyze reactions (e.g., hydrocarbon conversion reactions), such as Co, Mo, V, Cu, Sn, Ga, Ge, Eu, and La. For element group designations, reference is made to the "CRC Handbook of Chemistry and Physics", 76$^{th}$ Edition (1995-1996), by David R. Lide, published by CRC Press, Inc. (USA), in which the groups of the periodic table are numbered 1 to 18. Representative matrix/binder materials, present in the substrate as described above, are selected from the group consisting of carbon, inorganic metal oxides, and mixtures thereof. Representative inorganic metal oxides include silica, alumina, titania, zirconia, vanadia, and boria, any of which may be present alone or as a mixed metal oxide.

The catalyst particle may be analyzed in ambient surroundings, in which the sample is exposed to air, or otherwise the relevant analytical information may be obtained on the catalyst particle in a surrounding fluid (e.g., gaseous, liquid, or 2-phase) environment that is representative of environments to which the catalyst particle is exposed in practice. Such environments include those encountered during normal service (e.g., in catalyzing a hydrocarbon conversion reaction), during a treatment (e.g., during reduction of the catalytic metals by exposure to a hydrogen-containing environment, during oxidation of the catalytic metals by exposure to an oxygen-containing environment, during oxychlorination or sulfiding of the catalyst by exposure to a chlorine- or sulfur-containing environment, etc.), or during regeneration (i.e., coke burn in an oxidative environment). In such environments, which differ from the ambient surroundings, the analytical data obtained from the methods described herein will generally differ, for example due to the different oxidation states of the dispersed element(s), and particularly the catalytic metal(s). When the sample is exposed to an environment other than the ambient surroundings, it may be placed in an enclosed ("in situ") cell approximating the environment to be studied.

Related to the analytical methods that allow characterization of macro-scale representative solids, particularly with respect to the localized environment of various elements (e.g., elements distributed in a dispersed phase and/or elements of a continuous phase), is the discovery of sample preparation methods that facilitate these methods. According to particular embodiments of the invention that relate to sample preparation, the solid material sample is combined with a reinforcing agent, and preferably such an agent that does not contain elements to be analyzed by x-ray absorption or fluorescence spectroscopy of the sample. These elements to be analyzed (i.e., elements of interest), which are namely the elements distributed in a solid substrate, and/or elements of the substrate itself (or elements of the matrix/binder of a solid catalyst sample), generally have absorption edge energies from about 300 eV to about 50,000 eV.

Preferably, the reinforcing agent does not contain any elements with adsorption edges or fluorescence lines within preferably about 1000 eV, and more preferably about 500 eV, in the case of XAS, of the element(s) to be analyzed (e.g., metals). Preferably, the reinforcing agent does not contain any elements with adsorption edges or fluorescence lines within about 50 eV, in the case of XRF, of the element(s) to be analyzed. According to other preferred embodiments, therefore, the reinforcing agent does not contain elements used to identify the substrate (or used to identify the matrix/binder of a solid catalyst particle) of the sample or otherwise does not contain the one or more elements to be probed with XAS. According to some embodiments, the reinforcing agent does not contain silicon, aluminum, and/or transition metals. According to yet further embodiments, the reinforcing agent does not contain elements having an adsorption edge energy of greater than about 1,000 eV. In some embodiments, both the reinforcing agent and the sample of solid material can both have some elements in common, for example carbon, oxygen, and/or nitrogen, that are not elements of interest. According to a specific embodiment, for example, oxygen is present both in the silica and/or alumina of a catalyst matrix/binder material, as well as in a polymer of a reinforcing agent such as an epoxy resin.

Preferably, the reinforcing agent contains elements (i.e., reinforcing agent elements) that are predominantly or all of a lower atomic number, relative to the dispersed elements and/or elements of the solid substrate to be analyzed. For example, the reinforcing agent may be a polymeric material (e.g., a thermosetting resin such as an epoxy resin) comprising predominantly carbon and further comprising minor amounts of one or more heteroatoms selected from O, N, S, and Si.

Aspects of the invention relate more particularly to the analysis of a sample of a formed solid catalyst having a high porosity and surface area. While these properties are necessary for effective reactant contacting in catalysis, they significantly complicate the conventional preparation of macroscale-representative samples of solid catalysts. For example, the porous nature of solid catalysts leads to disintegration of the catalyst structure, when cut to a sufficiently small thickness dimension to allow meaningful characterization by spatially resolved x-ray spectroscopy in either the fluorescence or transmission mode. Conventional analysis of solid catalysts by x-ray spectroscopy has therefore been performed on ground and well mixed catalyst powder samples (representative of the bulk composition), rather than a macroscale-representative sample. Advantageously, the methods described herein with macroscale-representative samples provide additional information related to material heterogeneity, discernable on such samples when analyzed over sufficiently large dimensions (e.g., exceeding tens of microns) in one or two dimensions.

This problem, however, is now effectively addressed by the sample preparation methods described herein, which are particularly applicable to solids having a substantial pore volume and/or surface area. Representative catalyst particles, for example, have a pore volume of generally greater than 0.2 cc/g (e.g., from about 0.2 to about 1.5 cc/g), typically greater than about 0.3 cc/g (e.g., from about 0.3 to about 1.3 cc/g), and often greater than about 0.4 cc/g (e.g., from about 0.4 to about 1.0 cc/g), as determined by mercury intrusion porosimetry, according to ASTM D4284-07. The majority of this pore volume is normally attributed to micropores having a pore size of less than 600 Å. The high pore volume of catalysts provides high surface areas, and representative catalyst particles therefore have a surface area generally within a range from about 50 to about 1000 $m^2/g$, typically from about 100 to about 650 $m^2/g$ and often from about 150 $m^2/g$ to about 400 $m^2/g$. Surface area is measured according to the Brunauer, Emmett and Teller (BET) method based on nitrogen adsorption (ASTM D1993-03 (2008)).

According to representative sample preparation methods, the reinforcing agent may be embedded in the solid, for example by being forced into its pores (e.g., by vacuum impregnation, which may be assisted by centrifugation). This manner of combining the reinforcing material and sample may occur prior to curing the reinforcing material. Impregnation and curing may be performed by initially placing the solid and reinforcing agent (e.g., in an uncured state) in a suitable housing such as a section of metal tubing, for example aluminum tubing that can be readily cut during subsequent sample preparation steps. As discussed above, combining a suitable reinforcing agent such as a polymeric material (e.g., an epoxy resin) with a solid such as a porous catalyst advantageously allows the solid to be cut to a sufficiently small dimension (e.g., thickness) for synchrotron x-ray analysis. Importantly, at least one macroscale dimension (e.g., length or diameter) of greater than about 100 μm in the sample is preserved, such that meaningful characteristics of the heterogeneity of the solid (e.g., the correlations between distributions and/or species of various elements) are maintained. The use of a reinforcing agent is therefore especially applicable to the analysis of porous, solid catalysts that otherwise cannot be cut to the desired dimensions (e.g., with an exemplary thickness dimension as described above, for example less than 100 μm, and an exemplary other dimension of greater than 100 μm) without mechanical degradation (e.g., crumbling).

Exemplary analytical methods therefore comprise preparing a macroscale-representative sample (i.e., a sample of the solid, such as a catalyst, where the sample is representative of the solid in terms of not only its bulk composition but also its heterogeneity). As discussed above, such a macroscale representative sample has at least one dimension (e.g., diameter), different from the thickness dimension, that is generally greater than about 100 μm in size (e.g., from about 100 μm to about 10 mm). Typically, this dimension at least about 500 μm in size (e.g., from about 500 μm to about 5 mm), and often it is at least about 1 mm in size (e.g., from about 1 mm to about 3 mm). Such samples, normally prepared as thin sections, may be mounted on a supporting structure that, like the reinforcing agent, preferably does not contain elements of interest (e.g., one or more of the distributed (dispersed) elements or one or more of the elements contained in the solid substrate). Other considerations relating to elements contained in the supporting structure are the same as those, discussed above, which apply to elements contained in the reinforcing agent.

Representative methods further comprise determining the distribution of the one or more elements from XRF analysis of the sample, as well as determining the speciation of the one or more elements from XAS analysis of the sample. The source of x-rays for both the XRF and XAS analyses is synchrotron radiation, which may be varied in energy over a wide range using a monochromator. The range of the generated spectra, which may include any energy level that is sufficient to ionize any element of the sample, is therefore generally from about 200 eV to about 35,000 eV. Typically, however, the energy level is within the range from about 5,000 eV to about 20,000 eV.

Representative methods described herein utilize a small, focused x-ray beam (i.e., microbeam) for XRF and XAS analysis. The x-ray beam size and the sample thickness determine the resolution of the technique. Representative x-ray beam sizes are generally less than about 10 µm (e.g., from about 1 nanometer (nm) to about 10 µm), and typically less than about 5 µm (e.g., from about 10 nm to about 5 µm). Depending on the particular application, it may be desirable to use x-ray beam sizes ranging from about 10 nm to about 500 nm. An important consideration is the ability to map a relatively large cross-sectional area of the sample of a formed, possibly heterogeneous, sample using microprobe XRF to determine spatial distribution of key elements. The area of mapping can be, for example, 100 nm to several millimeters in size (e.g., in one dimension or in diameter), and typically this dimension exceeds the beam size by a factor of 50-100. The spatial maps are then used to determine locations for further investigation using XAS technique at single locations or at several locations to map the speciation.

As noted above, XAS includes both EXAFS and XANES. EXAFS or XAFS gives information about the atomic coordination environment of the element of interest. XANES gives information about the valence state and coordination geometry (tetragonal, octahedral, square bi-planar, etc.) of the element of interest. XRF gives information on what elements are present and their quantities. XRF, however, does not require a monochromatic beam or the ability to change the energy of the x-ray beam, as XAS does. For high quality XAS measurements, elements of interest typically have absorption edges between 300 eV and 50,000 eV, and usually less than 30,000 eV. These absorption edges can be K-edges, L-edges, or M-edges. Usually, the absorption edges are K-edges, but are sometimes L-edges or M-edges. The absorption edge is preferably isolated from other fluorescent lines from the sample and binder. About −150 to 250 eV (−20 eV to 20 eV at least) is generally required, relative to the edge energy for XANES and at least to about 1000 eV above the edge energy for EXAFS, although in some embodiments this value could be as low as only to about 600 eV above the edge energy.

The materials and samples described herein (e.g., catalysts and catalyst samples) can have varying elements of interest. In the case of catalysts, these include elements that are specific to the matrix/binder material that will help identify these regions by using XRF. It is possible to purposefully put tracers, for example Fe, into different components including the binder to identify pore regions. In some cases, the concentration of an element in the binder/matrix can differ significantly from one region to the next, such that these different regions are identifiable. Thus, the presence and possibly the amount of an element can be used identify the metal support material. Other key elements may also be probed with XAS, and these are often the catalytically active metal centers (sites), but these could also be trace elements, such as C, deposited from a hydrocarbon feedstock or trace metals (Fe), deposited from the wall of a reactor. Other metals could be those that migrate from the binder/matrix during catalyst use. It is important to correlate the location of the key XAS elements with elements of the support material and it is important to determine the XAS information from those key elements. Generally, as long as the "high quality XAS measurement" criteria can be met, all the other atoms in the sample/binder are considered to have little or no importance.

The following examples are set forth as representative of the present invention. These examples are not to be construed as limiting the scope of the invention as other equivalent embodiments will be apparent in view of the present disclosure and appended claims.

Example 1

Macroscale-Representative Catalyst Sample Preparation and Analytical Equipment

Samples of cylindrical extruded particles (extrudates) of catalysts comprising cobalt and molybdenum (as catalytically active metals) dispersed on an alumina-containing substrate were prepared for analysis by x-ray fluorescence (XRF) and x-ray absorption spectroscopy (XAS). A "prototype" catalyst differed from a "reference" catalyst in that it contained amorphous silica alumina, available commercially from Catalysts & Chemicals Industries Co. Ltd. (CCIC) (Yokohama, Japan), in the catalyst substrate. In each case, the catalyst particles were combined with an EPON™ epoxy resin (Miller-Stephenson Chemical Company, Inc., Danbury, Conn., USA) as a reinforcing agent, by embedding the particles in the resin, which, with the exception of Cl, contained elements all of a lower atomic number relative to those of interest in the solid catalyst particle samples being analyzed. To force the epoxy resin into the catalyst pores and thereby prevent crumbling of the extrudates upon cutting, vacuum impregnation was performed. In this process, the extrudates were placed in a polyethylene PE capsule immersed in the epoxy resin. Vacuum pressure was then applied, followed by venting to mitigate bubble formation.

Following the vacuum impregnation, the extrudates were set in short pieces of aluminum tubing, having one end affixed to a teflon block. The tube pieces were then back-filled with additional epoxy and evacuated again, followed by additional back-filling. The epoxy was then cured overnight, and thereafter the extrudate-containing tube pieces were gently pried away from the teflon. These pieces were then sawed into small cylindrical sections that were positioned on a steel polishing mount, using a metallographic mounting wax (thermal wax). The cylindrical sections were ground and polished to obtain sample thicknesses uniformly below 100 µm.

For analysis, a cylindrical section, now containing the macroscale-representative sample of the solid to be analyzed, was then oriented in an appropriate micro-positioning stage at the synchrotron beamline. The x-ray beam was focused using a method appropriate for providing an x-ray beam of suitable diameter, in this case using Kirkpatrick-Baez mirrors. Elemental maps were collected from an x-ray fluorescence detector. In particular, elemental concentration maps, obtained using XRF, were processed using image analysis software. In addition to the x-ray fluorescence, x-ray absorption spectra were also collected in fluorescence mode. More particularly, x-ray absorption near edge structure (XANES) data were analyzed using standard analysis packages.

Example 2

Analysis of the Macroscale-Representative Catalyst Samples by XRF and XAS

The results of the XRF and XAS analyses for the prototype catalyst, having a substrate comprising both alumina and amorphous silica alumina, were compared to those of the reference catalyst, without the amorphous silica alumina. The relative distributions of Co, Mo, Si (of the CCIC particles) and Fe (of the alumina binder) were determined from XRF to produce 2-dimensional elemental specific maps, covering a sample area of 400×500 μm, for the prototype and reference catalysts, as shown in FIG. 1. A specific finding from this analysis of the macroscale-representative samples (which could not be determined from analysis of bulk powder samples) was the heterogeneity in both Mo and Co distribution that result from the introduction of amorphous silica alumina in the catalyst substrate. Also evident from the XRF results was a positive correlation between regions of low Mo concentration and regions of high amorphous silica alumina concentration, indicating a preference of Mo for the alumina.

Figure 2A:
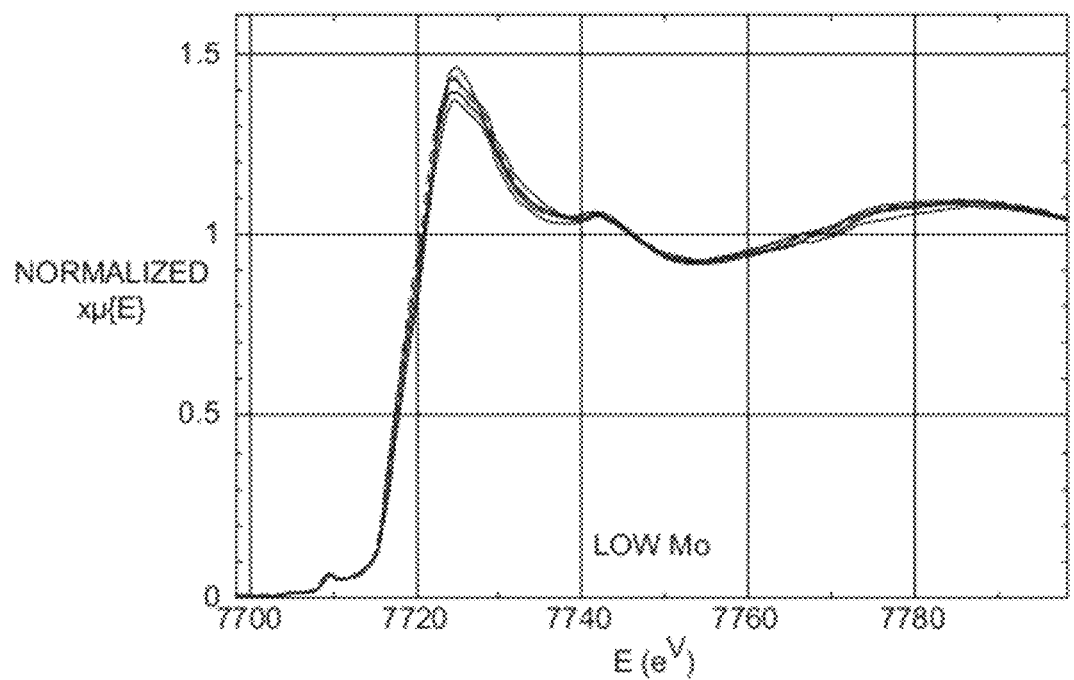
FIGS. 2A and 2B provide x-ray absorption spectra, and particularly the Co K-edge x-ray absorption near edge structure (XANES) spectra of the catalyst samples described with respect to FIG. 1. The XANES spectra were compared for several discreet micron sized locations of high and low concentrations of molybdenum, as determined on the micron length scale according to the processed XRF images shown in FIG. 1.
Figure 2A:
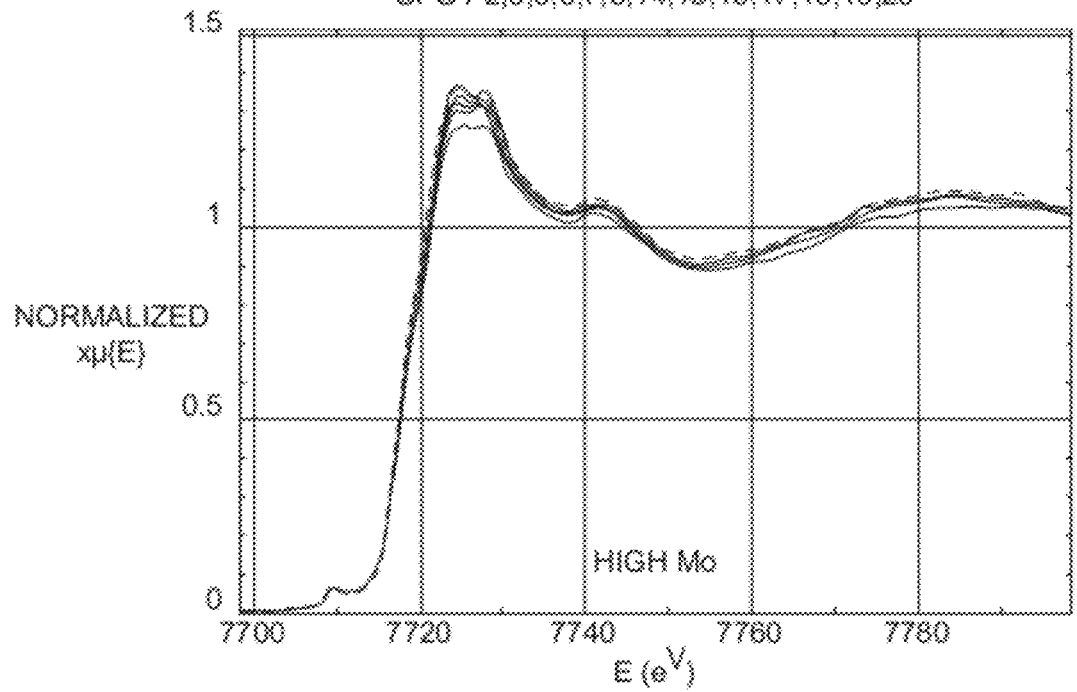
Figure 2B:
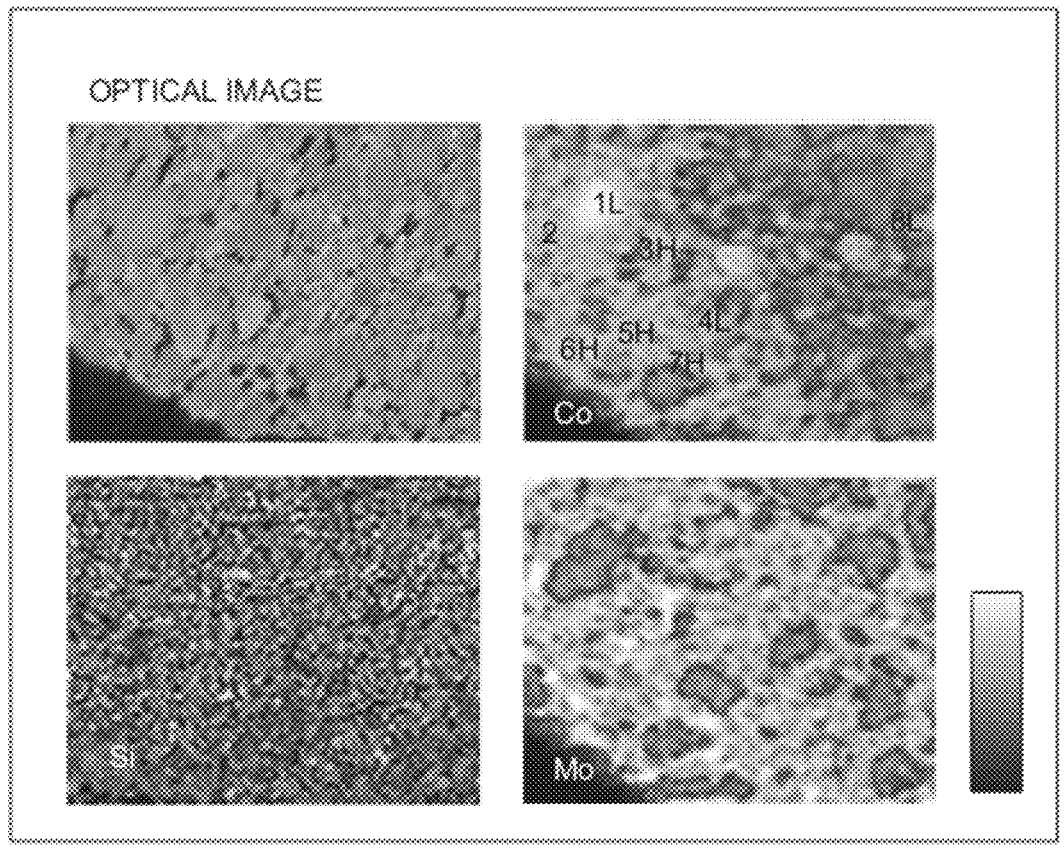
Figure 2B:
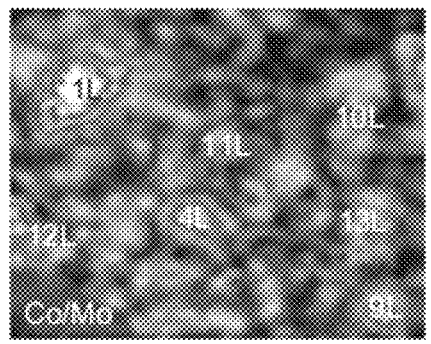
Figure 2B:
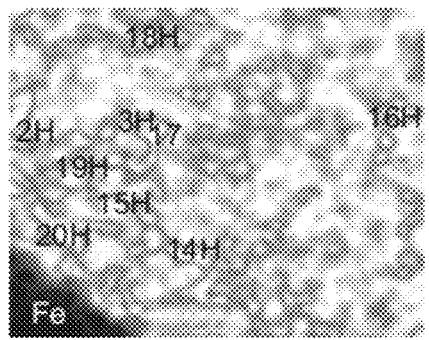

The analysis of the XRF maps, when combined with the XANES spectra, yielded yet more information, specific to the heterogeneity of the solid samples, which could only be observed with macroscale-representative catalyst samples used in this experimentation. In particular, based on the XANES spectra of Co, this element was present in the alumina structure (as $CoAlO_4$) in regions of high alumina concentration (determined from XRF mapping), whereas it was present in sulfided form in regions of high amorphous silica alumina concentration (also determined from XRF mapping). The differing XANES spectra shown in FIGS. 2A and 2B further illustrate how elements in regions of high or low concentration (determined from XRF mapping) can be correlated with different elemental species (e.g., different oxidation states, bonded atoms, and/or coordination geometry). Overall, these results show that the introduction of amorphous silica alumina in the catalyst substrate leads to heterogeneity in both the Mo distribution and in the Co speciation. Obtaining such valuable information in solids characterization is made possible using macroscale-representative sample preparation, combined with spatially resolved XRF analysis to determine elemental compositions and amounts and spatially resolved XAS (x-ray absorption near edge structure) spectra in fluorescence modes, according to the methods described herein.

The invention claimed is:

1. A method for analyzing a solid comprising one or more elements distributed in a solid substrate, the method comprising:
   (a) preparing a sample of the solid, wherein the sample is combined with a reinforcing agent that does not contain the one or more elements;
   (b) obtaining the distribution of the one or more elements from spatially resolved x-ray fluorescence (XRF) analysis of the sample, and
   (c) obtaining the speciation of the one or more elements from spatially resolved x-ray absorption spectroscopy (XAS) analysis of the sample,
   wherein the source of x-rays for steps (b) and (c) is synchrotron radiation;
   wherein the macroscale-representative samples are macroscale-representative of the solid over at least one dimension or over two dimensions;
   wherein the macroscale-representative sample has a thickness from about 10 μm to about 500 μm;
   wherein the macroscale-representative sample thickness is commensurate to the spatial resolution and the penetration depth of x-rays; and
   wherein the reinforcing agent is embedded in the sample by vacuum impregnation.

2. The method of claim 1, wherein the photon energy synchrotron radiation is varied using a monochromator.

3. The method of claim 1, wherein the XAS analysis comprises x-ray absorption fine structure (XAFS), extended x-ray absorption fine structure (EXAFS), x-ray absorption near edge structure (XANES), or a combination thereof.

4. The method of claim 1, wherein the solid is a catalyst particle.

5. The method of claim 4, wherein the sample is in an atmosphere comprising predominantly a fluid to which the catalyst particle is exposed during normal service, during treatment, or during regeneration.

6. The method of claim 4, wherein the catalyst particle is cylindrical or spherical.

7. The method of claim 1, wherein the reinforcing agent contains reinforcing agent elements that are predominantly of a lower atomic number, relative to the one or more elements or solid substrate elements.

8. The method of claim 1, wherein the reinforcing agent is a polymeric material.

9. The method of claim 1, wherein the one or more elements are metals.

10. The method of claim 9, wherein the one or more elements are metals of any of Groups 4-13 of the Periodic Table.

11. The method of claim 1, wherein the solid substrate comprises carbon or an inorganic metal oxide.

12. The method of claim 11, wherein the solid substrate comprises carbon or a metal oxide selected from the group consisting of silica, alumina, titania, zirconia, and mixtures thereof.

13. The method of claim 1, wherein step (b) comprises analyzing a 2-dimensional elemental specific XRF map of the sample.

14. The method of claim 1, wherein step (b) comprises obtaining the distribution of one or more components of the solid substrate.

15. The method of claim 14, wherein step (b) further comprises (i) correlating the distribution of the one or more elements with the distribution of the one or more components of the solid substrate or (ii) correlating the speciation of the one or more elements with the distribution of the one or more components of the solid substrate.

16. The method of claim 1, wherein step (c) comprises determining the oxidation state of the one or more elements, atoms bonded to the one or more elements, or the coordination geometry of the one or more elements.

* * * * *